United States Patent [19]

Conley et al.

[11] 4,252,945
[45] Feb. 24, 1981

[54] PROCESS FOR PREPARING PYRAZOLO[1,5-C]-QUINAZOLINE DERIVATIVES AND NOVEL INTERMEDIATES

[75] Inventors: Richard A. Conley, Annandale, N.J.; Margaret M. Lam, New York, N.Y.; LeRoy B. High, Cranbury, N.J.

[73] Assignee: E. R. Squibb & Sons, Inc., Princeton, N.J.

[21] Appl. No.: 56,660

[22] Filed: Jul. 11, 1979

[51] Int. Cl.³ .......................................... C07D 487/04
[52] U.S. Cl. .................... 544/250; 546/153; 546/155; 560/20; 560/38; 560/39
[58] Field of Search ........................................ 544/250

[56]  References Cited
U.S. PATENT DOCUMENTS

| | | | |
|---|---|---|---|
| 3,313,815 | 4/1967 | Wolfe et al. | 544/250 |
| 3,899,508 | 8/1975 | Wikel | 548/378 |
| 4,035,368 | 7/1977 | Erickson | 546/153 |
| 4,076,818 | 2/1978 | Vogt | 424/251 |
| 4,107,167 | 8/1978 | Lorenz et al. | 546/156 X |
| 4,112,096 | 9/1978 | Vogt | 424/251 |
| 4,119,720 | 10/1978 | Hardtmann | 424/258 |
| 4,145,420 | 3/1979 | Vogt | 424/248.5 |

OTHER PUBLICATIONS

Kirk-othmer, Encyclopedia of Chemical Technology, vol. 8, pp. 472-473, John Wiley & Sons, Inc. (1965).
Fieser, et al., Reagents for Organic Synthesis, John Wiley & Sons, New York, 1967, pp. 451, 1024.
Fieser, et al., Reagents for Organic Synthesis, vol. 4, John Wiley & Sons, New York, 1974, p. 250.
Noller, Chemistry of Organic Compounds, 3rd ed., W. B. Saunders Co., Philadelphia, 1965, pp. 183-186.

Primary Examiner—Donald G. Daus
Assistant Examiner—Diana G. Rivers
Attorney, Agent, or Firm—Lawrence S. Levinson; Burton Rodney

[57] ABSTRACT

A process is provided for preparing pyrazolo-[1,5-c]quinazoline derivatives of the structure

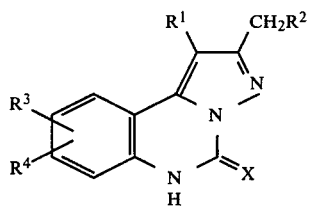

wherein X is O or S; $R^1$ is hydrogen, lower alkyl, hydroxymethyl, phenyl-lower alkyl, phenyl or phenyl substituted with halogen, lower alkyl, lower alkoxy, or trifluoromethyl; $R^2$ is lower alkoxy, phenyl-lower alkoxy, phenoxy, or phenoxy substituted with lower alkyl or lower alkoxy; and $R^3$ and $R^4$ are the same or different and are selected from the group consisting of hydrogen, alkyl of 1 to 4 carbons, alkoxy of 1 to 4 carbons, lower alkanoyloxy of 1 to 4 carbons, nitro, benzyloxy, benzyloxy having a single monolower alkoxy substituent, halogen, hydroxy, and trifluoromethyl, wherein quinolone compounds of the structure

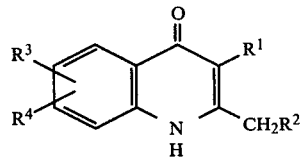

which are new intermediates, are reacted with a hydrazine compound to form a 5-(2-aminophenyl)-pyrazole which is then cyclized to the product.

In addition, the above product may be reacted with a halogen acid to form the corresponding hydroxymethyl compound.

22 Claims, No Drawings

PROCESS FOR PREPARING PYRAZOLO[1,5-c]-QUINAZOLINE DERIVATIVES AND NOVEL INTERMEDIATES

BRIEF DESCRIPTION OF THE INVENTION

The present invention relates to a process for preparing pyrazolo[1,5-c]quinazolines of the structure

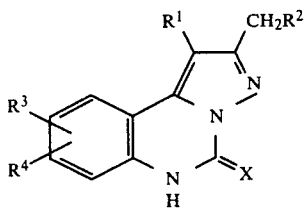

wherein
X is O or S;
$R^1$ is hydrogen, lower alkyl, hydroxymethyl, phenyl-lower alkyl, phenyl or phenyl substituted with halogen, lower alkyl, lower alkoxy, or trifluoromethyl;
$R^2$ is lower alkoxy, phenyl-lower alkoxy, phenoxy, or phenoxy substituted with lower alkyl or lower alkoxy;
$R^3$ and $R^4$ are the same or different and are selected from the group consisting of hydrogen, alkyl of 1 to 4 carbons, alkoxy of 1 to 4 carbons, lower alkanoyloxy of 1 to 4 carbons, nitro, benzyloxy, benzyloxy having a single mono-lower alkoxy substituent, halogen, hydroxy, and trifluoromethyl.

The present invention also related to a process for preparing pyrazolo[1,5-c]quinazolines of the structure

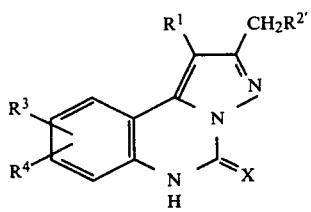

wherein $R^1$, $R^3$, $R^4$ and X are as defined above and $R^{2'}$ is $CH_2OH$ or $CH_2Hal$ wherein Hal is Cl, Br or F, and which process may also include the preparation of compounds of the structure

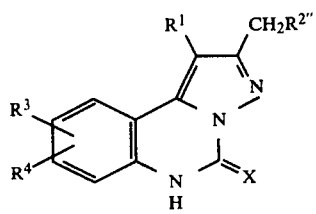

wherein $R^1$, $R^3$, $R^4$ and X are as defined above and $R^{2''}$ is lower alkanoyloxy, phenyl-lower alkanoyloxy or benzyloxy.

Essentially all of the above pyrazolo[1,5-c]quinazolines are disclosed in U.S. Pat. Nos. 4,076,818 and 4,112,096, as well as in U.S. application Ser. No. 900,050, filed Apr. 26, 1978, and are useful as antiallergy agents.

In addition, novel intermediates are also provided which are prepared in the course of carrying out the processes of the invention and have the structures

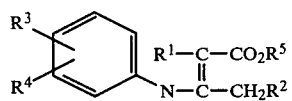

and

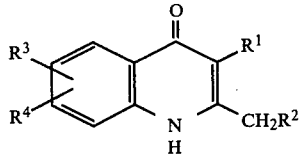

wherein $R^1$, $R^2$, $R^3$ and $R^4$ are as defined above and $R^5$ is lower alkyl.

DETAILED DESCRIPTION OF THE INVENTION

Unless otherwise indicated the term "lower alkyl" or "alkyl" as employed herein includes both straight and branched chain radicals of up to eight carbon atoms, for instance, methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, and the like.

Unless otherwise indicated, the term "lower alkoxy" or "alkoxy" includes straight and branched chain radicals which correspond to the above lower alkyl groups attached to an oxygen atom.

Unless otherwise indicated, the term "lower alkanoyl" or "alkanoyl" as employed herein includes any of the above lower alkyl groups linked to a carbonyl group.

Unless otherwise indicated, the term "substituted phenyl" includes radicals, such as lower alkyl phenyl (e.g., o-, m- or p-tolyl, ethylphenyl, butylphenyl, and the like), di(lower alkyl)phenyl (e.g., 2,4-dimethylphenyl, 3,5-diethylphenyl, and the like), halophenyl (e.g., chlorophenyl, bromophenyl, iodophenyl, fluorophenyl), lower alkoxyphenyl (e.g., methoxyphenyl or ethoxyphenyl); or trifluoromethylphenyl.

Unless otherwise indicated, the term "lower alkanoyloxy" or "alkanoyloxy" as employed herein includes any of the above defined "lower alkanoyl" or "alkanoyl" groups linked to an oxygen atom.

The process in accordance with the present invention for preparing the formula I compounds

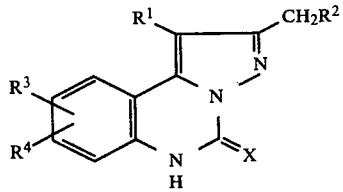

includes the steps of reacting a quinolone compound of the structure

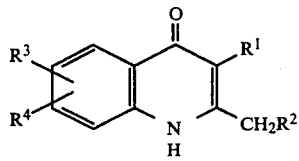

with a hydrazine compound, preferably a hydrazine dihydrohalide, such as hydrazine dihydrochloride, and hydrazine, in the presence of a high boiling solvent (for example, boiling at above about 150° C.), such as ethylene glycol or anisole, to form a 5-(2-aminophenyl)-pyrazole of the structure VI

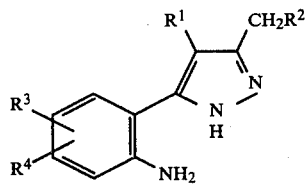

wherein $R^1$, $R^2$, $R^3$ and $R^4$ are as defined above, employing the procedures similar to those outlined in U.S. Pat. No. 3,313,815; Bowie et al, *J. Chem. Soc. Perkin I*, 1972, 1106; Field et al, *J. Org. Chem.*, 36, 2968 (1971); de Stevens et al, *Angew. Chemie*, 74, 249 (1962); and Alberti, *Gazz. Chim. Ital.*, 87, 772 (1957).

The above reaction is preferably carried out at a temperature of from about 150° to about 230° C., more preferably from about 160° to about 180° C., for a period ranging from about 3 to about 24 hours, more preferably from about 3 to about 6 hours, employing a molar ratio of V:hydrazine compound of from about 0.05:1 to about 1:1, more preferably from about 0.05:1 to about 0.2:1.

The 5-(2-aminophenyl)-pyrazole VI is then cyclized by reaction with a cyclizing agent of the structure VII VII  CXCl₂ where X is O or S (that is, phosgene or thiophosgene) or ethyl chloroformate, to form a pyrazolo[1,5-c]quinazoline of the structure I, employing procedures similar to those outlined in U.S. Pat. Nos. 3,531,482, 3,313,815 and 3,899,508, as well as in de Stevens et al, *J. Org. Chem.* 28, 1336 (1963), and the de Stevens et al, Field et al, and Bowie et al references mentioned above. The latter reaction is carried out in the presence of a basic solvent such as pyridine, triethylamine, quinoline, dimethylaniline and the like, at a temperature ranging from about 60° to about 240° C., more preferably from about 80° to about 120° C., for a period ranging from about 3 to about 24 hours and more preferably from about 12 to about 24 hours employing a molar ratio of VI to cyclizing agent of from about 0.2:1 to about 1:1, and more preferably from about 0.3:1 to about 1:1.

In preferred embodiments of the invention, the starting quinolone V will have the following structure

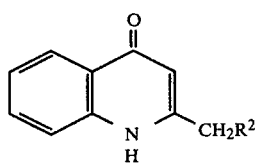

and the cyclizing agent preferably employed will be phosgene, so that the final products of structure I will have the following structure

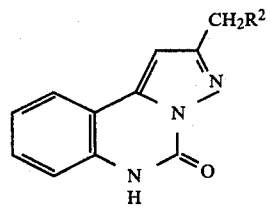

The compounds of formula II which include a $CH_2R^{2'}$ group at the 2-position, representing $CH_2OH$ or $CH_2Hal$, are prepared, in accordance with the present invention, by reacting a compound of formula I with a halogen acid such as HBr, HCl or HF, preferably in a molar ratio of I:halogen acid of within the range of from about 0.01:1 to about 1:1, and more preferably from about 0.03:1 to about 0.06:1. The above reaction may be carried out at a temperature of from about 20° to about 130° C., and more preferably from about 80° to about 120° C. and most preferably at reflux temperature for periods of about 30 minutes or less to ensure a larger proportion of hydroxymethyl compound IIa

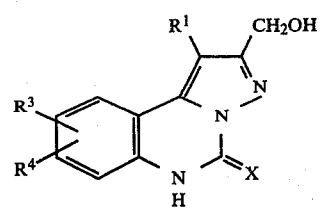

and a smaller proportion of halomethyl compound IIb

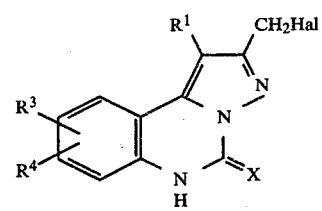

Such reaction may be carried out for a period of from about 15 minutes to about 4 hours, and preferably from about 30 minutes to about 1 hour.

In accordance with the process of the invention, a mixture of the compounds IIa and IIb may be converted to the more desirable compound IIa by simply heating the mixture at a temperature ranging from about 20° to about 100° C., and preferably from about 80° to about 100° C., in the presence of water, for periods of from about 1 hour to about 24 hours and preferably from about 4 to about 6 hours.

Alternatively, the mixture of compounds IIa and IIb may be converted to the more desirable compound IIa by reacting the mixture of compounds IIa and IIb with an alkali metal compound $MR^{2''}$   VIII wherein M is an alkali metal and $R^{2''}$ is lower alkanoyloxy, phenyl-lower alkanoyloxy or benzoyloxy, and the corresponding carboxylic acid $$R^{2''}H \qquad \text{IX}$$

wherein $R^{2''}$ is as above, to form the formula III compound

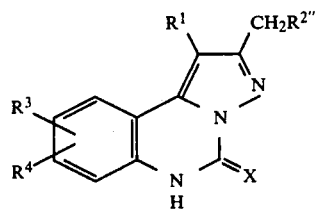

or

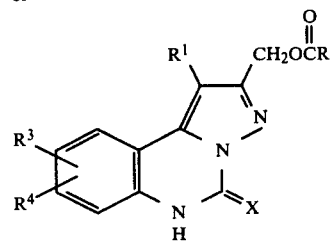

where R is lower alkyl, phenyl or phenyl-lower alkyl.

The latter reaction is preferably carried out at a temperature ranging from about 20° to about 150° C., and more preferably from about 80° to about 120° C., for a period of from about 1 to about 24 hours and preferably from about 10 to about 16 hours. The compound IIa preferably will be employed in a molar ratio to compound IX of within the range of from about 0.01:1 to about 0.1:1, and more preferably from about 0.03:1 to about 0.05:1, while the compound IIb will be employed in a molar ratio to compound VIII within the range of from about 0.2:1 to about 1:1, and more preferably from about 0.4:1 to about 0.5:1.

The formula III or IIIa compound may be converted to the hydroxymethyl compound of formula IIa by simply reacting the formula III or IIIa compound with a strong base, such as sodium hydroxide or potassium hydroxide, in the presence of a lower alkanol solvent, such as methanol or ethanol, (molar ratio of base:alkanol, preferably being from about 0.5:1 to about 0.1:1) for a period ranging from about 3 to about 24 hours and preferably from about 3 to about 6 hours and thereafter neutralizing the reaction mixture with a concentrated mineral acid, such as hydrochloric acid or sulfuric acid.

The quinolone starting material V is a new compound and may be prepared by reacting an aniline compound X

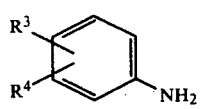

wherein $R^3$ and $R^4$ are as defined above with a carboxylic acid ester of the structure XI

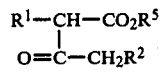

wherein $R^1$ and $R^2$ are as defined above and $R^5$ is lower alkyl, in a molar ratio of X:XI preferably of 1:1 to form an intermediate of the structure IV

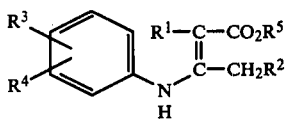

wherein $R^1$, $R^2$, $R^3$, $R^4$ and $R^5$ are as defined above. The above reaction is preferably carried out in the presence of a weak organic acid, such as acetic acid or propionic acid, and an aromatic solvent such as benzene or toluene, or hexane at a temperature ranging from about 60° to about 120° C. and preferably from about 60° to about 80° C. for a period of from about 1 hour to about 12 hours and preferably from about 2 to about 3 hours.

As indicated, the intermediate IV represents a new compound and as such forms a part of the present invention.

The quinolone compound V (also a new intermediate) is then prepared by simply reacting the intermediate IV with diphenyl ether in a molar ratio of IV:ether of from about 0.1:1 to about 0.5:1, and preferably from about 0.1:1 to about 0.2:1, at a temperature ranging from about 180° to about 270° C., and preferably from about 240° to about 260° C. for a period of from about 30 minutes to about 2 hours, and preferably from about 30 minutes to about 1 hour.

In a preferred embodiment, aniline itself (the formula X compound) is reacted with the carboxylic acid ester

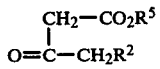

so that the intermediate IV will have the structure

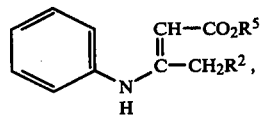

and the quinolone V produced will have the structure Va.

The carboxylic acid ester starting material XI may be prepared as described in U.S. Pat. No. 3,775,467.

Alternatively, the formula V quinolone may be prepared by reacting an isatoic anhydride

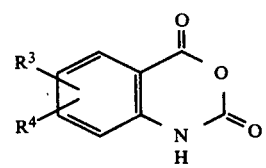

with a carboxylic acid ester XI, in a molar ratio of XII:XI of from about 0.5:1 to about 1:1, and preferably about 1:1 in the presence of an inert solvent such as tetrahydrofuran or dioxane, and a strong base such as sodium or potassium hydroxide, at a temperature ranging from about 40° to about 100° C., and preferably from about 60° to about 70° C. to form a compound of the structure XIII

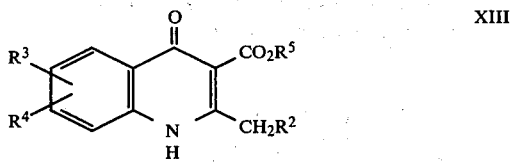

which is then hydrolyzed and neutralized to form the corresponding carboxylic acid XIV

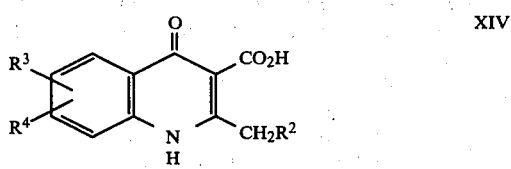

which is then decarboxylated at a temperature ranging from about 180° to about 300° C. and preferably from about 240° to about 260° C. to the formula V quinolone.

The following Examples represent preferred embodiments of the present invention.

EXAMPLE 1

β-Anilino-γ-methoxycrotonate

A solution containing 9.3 g (0.1 mol) of aniline, 14.6 g (0.1 mol) of methyl γ-methoxyacetoacetate and 1 ml of acetic acid in 100 ml of benzene is refluxed for 3 hours with azeotropic removal of water. Evaporation under reduced pressure gives 21.8 g (95%) of the crude β-anilino-γ-methoxycrotonate.

EXAMPLE 2

2-Methoxymethyl-4-quinolone

The crude crotonate (21.2 g/0.096 mol) from Example 1 is added over a 30 minute period to 75 ml of refluxing diphenyl ether. The reaction mixture is refluxed for 30 minutes, cooled, and 300 ml of hexane added. The resulting crude product is filtered, washed three times with 150 ml of hexane and dried overnight under vacuum at 60° C. Recrystallization of the crude product (15.2 g/83.5%) from water with Darco treatment gives 10.6 g (58.2%) of 2-methoxymethyl-4-quinolone as creme-colored needles, m.p. 183.5°–185.0° C.

EXAMPLE 3

2-Methoxymethylpyrazolo[1,5-c]quinazoline-5-one

A. 5-(2-Aminophenyl)-3-methoxymethylpyrazole

A mixture of 7.5 g (0.04 mol) of 2-methoxymethyl-4-quinolone, 4.2 g (0.04 mol) of hydrazine dihydrochloride, 12.8 ml (0.4 mol) of 95% hydrazine and 30 ml of ethylene glycol is slowly heated to reflux. The resulting solution is refluxed for 5 hours, cooled, diluted with 200 ml of distilled water, and extracted twice with methylene chloride (1×400 ml, 1×200 ml). The combined methylene chloride extracts are washed with 100 ml of distilled water, dried over sodium sulfate, and evaporated to 8.0 g of clear oil. Trituration with 25 ml of hexane gives 6.95 g (86%) of the 5-(2-aminophenyl)-3-methoxymethylpyrazole as a white powder, m.p. 74.0°–78.0° C.

B. 2-Methoxymethylpyrazolo[1,5-c]quinazoline-5-one

A solution of 4.9 g (0.024 mol) of 5-(2-aminophenyl)-3-methoxymethylpyrazole in 135 ml of pyridine is prepared and 55 ml of a 12.5% phosgene in benzene solution is slowly added. After refluxing 22 hours, the reaction is cooled, diluted with 50 ml of distilled water, and evaporated to a dark black paste. Distilled water (200 ml) is added and the reaction mixture is extracted with methylene chloride (2×300 ml). The combined methylene chloride layers are washed with 1 N HCl (2×200 ml) and distilled water (2×200 ml). After drying over sodium sulfate, evaporation gives the crude product which is recrystallized with Darco treatment from acetonitrile to give 2.76 g (49%) of the desired ether, m.p. 192.5°–195.0° C.

EXAMPLE 4

Mixture of 2-Bromo-methylpyrazolo[1,5-c]quinazoline-5-one and 2-Hydroxymethylpyrazolo[1,5-c]quinazoline-5-one A mixture of 1.1 g (0.0048 mol) of 2-methoxypyrazolo[1,5-c]quinazoline-5-one and 15 ml of 48% HBr is refluxed for 30 minutes, cooled, and diluted by the addition of 100 ml of cracked ice and 100 ml of distilled water. The crude product is filtered and washed with 2×25 ml of cold distilled water. TLC and NMR show the crude product (1.03 g) to be a mixture of 2-hydroxymethylpyrazolo[1,5-c]quinazoline-5-one and 2-bromo-methylpyrazolo[1,5-c]quinazoline-5-one.

EXAMPLE 5

2-Acetyloxymethylpyrazolo[1,5-c]quinazoline-5-one

The crude product (0.9 g) from Example 4 is refluxed with 0.3 g of sodium acetate in 18 ml of acetic acid for 15.5 hours. The reaction mixture is cooled, evaporated, dissolved in 50 ml of distilled water, and extracted with methylene chloride 1×100 ml, 1×50 ml). The combined methylene chloride layers are washed with 100 ml of distilled water, dried over sodium sulfate, and evaporated to 1.01 g (81.5%) of fluffy white 2-acetyloxymethylpyrazolo[1,5-c]quinazoline-5-one, m.p. 186.0°–187.0° C.

EXAMPLE 6

2-Hydroxymethylpyrazolo[1,5-c]quinazoline-5-one

The crude acetate product from Example 5 is slurried in a solution of 0.3 g of sodium hydroxide in 10 ml of aqueous methanol (1:1). After stirring for 5 hours, the reaction mixture is neutralized with concentrated hydrochloric acid followed by the addition of 13 ml of distilled water. After stirring overnight, the product is filtered, washed with cold distilled water and dried under vacuum at 60° C. to 0.62 g (72%) of white product, m.p. 285.0°–288.0° C.

EXAMPLES 7 TO 24

Following the procedure of Examples 1 and 2 except substituting the aniline compound shown in Column I of Table A below and substituting the carboxylic acid ester shown in Column II, the intermediates shown in Columns III and IV are obtained.

TABLE A

| | Column I | | Column II | | |
|---|---|---|---|---|---|
| Ex. No. | $R^3$(position) | $R^4$(position) | $R^1$ | $R^2$ | $R^5$ |
| 7. | $CH_3(2)$ | H | H | $C_2H_5O$ | $CH_3$ |
| 8. | F(4) | H | $CH_3$ | $C_6H_5-CH_2O$ | $CH_3$ |
| 9. | Cl(2) | $CH_3O(4)$ | $C_2H_5$ | $C_6H_5O$ | $C_2H_5$ |
| 10. | $CH_3\overset{O}{\overset{\|}{C}}O(4)$ | H | $CH_2OH$ | $CH_3O$ | $C_2H_5$ |
| 11. | $C_6H_5-CH_2O(4)$ | H | $C_6H_5CH_2$ | $CH_3O$ | $CH_3$ |
| 12. | $C_2H_5(3)$ | $C_2H_5(4)$ | $C_6H_5$ | $C_2H_5O$ | $CH_3$ |
| 13. | $CF_3-C_6H_4$ | H | H | $C_6H_5O$ | $C_2H_5$ |
| 14. | H | H | H | $p$-$CH_3$-$C_6H_4O$ | $n$-$C_3H_7$ |
| 15. | H | H | $CH_3$ | $m$-$CH_3O$-$C_6H_4O$ | $i$-$C_3H_7$ |

| | Column III | | | | | Column IV | | | |
|---|---|---|---|---|---|---|---|---|---|
| Ex. No. | $R^3$ (position) | $R^4$ (position) | $R^1$ | $R^2$ | $R^5$ | Ex. No. | $R^3$ (position) | $R^4$ (position) | $R^1$ $R^2$ |
| 7. | as in Column I | | as in Column II | | | 16. | $CH_3(8)$ | H | as in Column II |
| 8. | | | | | | 17. | F(6) | H | |
| 9. | | | | | | 18. | Cl(8) | $CH_3O(6)$ | |
| 10. | | | | | | 19. | $CH_3\overset{O}{\overset{\|}{C}}(6)$ | H | |
| 11. | | | | | | 20. | $C_6H_5-CH_2O(6)$ | H | |
| 12. | | | | | | 21. | $C_2H_5(7)$ | $C_2H_5(6)$ | |
| 13. | | | | | | 22. | H | H | |
| 14. | | | | | | 23. | H | H | |
| 15. | | | | | | 24. | H | H | |

EXAMPLES 25 TO 33

Following the procedure of Example 3 except substituting the quinolones of Examples 16 to 24, Column IV, Table A for 2-methoxymethyl-4-quinoline, (shown in Column I of Table B below), and the cyclizing agent shown in Column II, the pyrazolo[1,5-c]quinazoline shown in Column III is obtained.

TABLE B

| | Column I | | | | Column II | Column III | | | | |
|---|---|---|---|---|---|---|---|---|---|---|
| Ex. No. | $R^3$ (position) | $R^4$ (position) | $R^1$ | $R^2$ | X | $R^3$ (position) | $R^4$ (position) | X | $R^1$ | $R^2$ |
| 25 | $CH_3(8)$ | H | H | $C_2H_5O$ | O | $CH_3(7)$ | H | as in Col. II | as in Col. I | |
| 26 | F(6) | H | $CH_3$ | $C_6H_5-CH_2O$ | S | F(9) | H | | | |
| 27. | Cl(8) | $CH_3O(6)$ | $C_2H_5$ | $C_6H_5O$ | O | Cl(7) | $CH_3O(9)$ | | | |
| 28. | $CH_3\overset{O}{\overset{\|}{C}}(6)$ | H | $CH_2OH$ | $CH_3O$ | S | $CH_3\overset{O}{\overset{\|}{C}}(9)$ | H | | | |
| 29. | $C_6H_5-CH_2O(6)$ | H | $C_6H_5CH_2$ | $CH_3O$ | O | $C_6H_5-CH_2O(9)$ | H | | | |
| 30. | $C_2H_5(7)$ | $C_2H_5(6)$ | $C_6H_5$ | $C_2H_5O$ | S | $C_2H_5(8)$ | $C_2H_5(9)$ | | | |
| 31. | H | H | H | $C_6H_5O$ | O | H | H | | | |
| 32. | H | H | H | $p$-$CH_3$-$C_6H_4O$ | S | H | H | | | |

TABLE B-continued

| | Column I | Column II | Column III |
|---|---|---|---|
| Ex. No. | $R^3$ (position) | $R^4$ (position) | $R^1$ | $R^2$ | X | $R^3$ (position) | $R^4$ (position) | X | $R^1$ | $R^2$ |
| 33. | H | H | $CH_3$ | m-$CH_3O$—$C_6H_4O$ | O | H | H | | | |

EXAMPLES 34 to 42

Following the procedure of Examples 4 and 5, except substituting the quinazoline of Examples 25 to 33 (shown in Column I of Table C below) and substituting for the sodium acetate and acetic acid, the salt and acid shown in Column II, the quinazoline shown in Column III is obtained.

EXAMPLES 43 TO 51

Following the procedure of Example 6 except substituting the quinazolines of Examples 34 to 42 (shown in Column I of Table D below), the corresponding hydroxymethyl compound shown in Column II is obtained.

TABLE C

| Ex. No. | $R^3$(position) | $R^4$(position) | X | $R^1$ | $R^2$ | R | M |
|---|---|---|---|---|---|---|---|
| 34. | $CH_3$(7) | H | O | H | $C_2H_5O$ | $CH_3$ | K |
| 35. | F(9) | H | S | $CH_3$ | $C_6H_5$—$CH_2O$ | $C_2H_5$ | Na |
| 36. | Cl(7) | $CH_3O$(9) | O | $C_2H_5$ | $C_6H_5O$ | $C_6H_5$ | Na |
| 37. | $CH_3\overset{O}{\underset{\|}{C}}$(9) | H | S | $CH_2OH$ | $CH_3O$ | $C_6H_5CH_2$ | Na |
| 38. | $C_6H_5$—$CH_2O$(9) | H | O | $C_6H_5CH_2$ | $CH_3O$ | n-$C_4H_9$ | K |
| 39. | $C_2H_5$(8) | $C_2H_5$(9) | S | $C_6H_5$ | $C_2H_5O$ | n-$C_3H_7$ | K |
| 40. | H | H | O | H | $C_6H_5O$ | $C_2H_5$ | Na |
| 41. | H | H | S | H | p-$CH_3$—$C_6H_4O$ | $CH_3$ | Na |
| 42. | H | H | O | $CH_3$ | m-$CH_3O$—$C_6H_4O$ | $C_2H_5$ | K |

Column III

| Ex. No. | $R^3$(position) | $R^4$(position) | $R^1$ | X | R |
|---|---|---|---|---|---|
| 34. | | | | | |
| 35. | | as in Column I | | | as in Column II |
| 36. | | | | | |
| 37. | | | | | |
| 38. | | | | | |
| 39. | | | | | |
| 40. | | | | | |
| 41. | | | | | |
| 42. | | | | | |

TABLE D

| Ex. No. | R³(position) | R⁴(position) | X | R¹ | R | R³(position) R⁴(position) R¹ X |
|---|---|---|---|---|---|---|
| 43. | CH₃(7) | H | O | H | CH₃ | as in Column I |
| 44. | F(9) | H | S | CH₃ | C₂H₅ | |
| 45. | Cl(7) | CH₃O(9) | O | C₂H₅ | C₆H₅ | |
| 46. | CH₃C(9)=O | H | S | CH₂OH | C₆H₅CH₂ | |
| 47. | C₆H₅—CH₂O(9) | H | O | C₆H₅CH₂ | n-C₄H₉ | |
| 48. | C₂H₅(8) | C₂H₅(9) | S | C₆H₅ | n-C₃H₇ | |
| 49. | H | H | O | H | C₂H₅ | |
| 50. | H | H | S | H | CH₃ | |
| 51. | H | H | O | CH₃ | C₂H₅ | |

What is claimed is:

1. A process for preparing pyrazolo[1,5-c]quinazolines of the structure

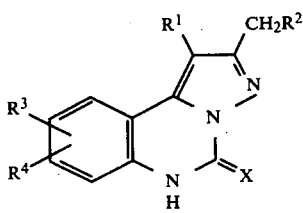

wherein X is O or S;
R¹ is hydrogen, lower alkyl, hydroxymethyl, phenyl-lower alkyl, phenyl or phenyl substituted with halogen, lower alkyl, lower alkoxy, or trifluoromethyl;
R² is lower alkoxy, phenyl-lower alkoxy, phenoxy, or phenoxy substituted with lower alkyl or lower alkoxy;
R³ and R⁴ are the same or different and are selected from the group consisting of hydrogen, alkyl of 1 to 4 carbons, alkoxy of 1 to 4 carbons, lower alkanoyloxy of 1 to 4 carbons, nitro, benzyloxy, benzyloxy having a single mono-lower alkoxy substituent, halogen, hydroxy, and trifluoromethyl;
and physiologically acceptable salts thereof, which comprises the steps of reacting a quinoline compound of the structure

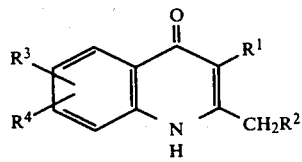

wherein R¹, R², R³ and R⁴ are as defined above, with a hydrazine compound to form a 5-(2-aminophenyl)pyrazole of the structure

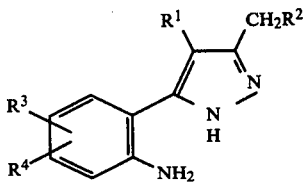

and thereafter reacting the above pyrazole with a cyclizing agent of the structure CXCl₂ or ethyl chloroformate to form the pyrazolo[1,5-c]quinazoline compound of the structure

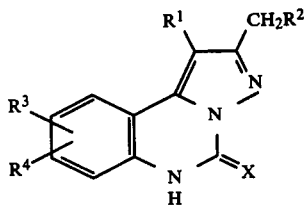

2. The process as defined in claim 1 wherein the hydrazine compound comprises hydrazine, hydrazine hydrohalide, or mixtures thereof, and is employed in a molar ratio to the quinolone starting material within the range of from about 0.05:1 to about 1:1.

3. The process as defined in claim 2 wherein the reaction of the hydrazine compound and the quinolone starting material is carried out at a temperature within the range of from about 150° to about 230° C. in the presence of an inert solvent.

4. The process as defined in claim 1 wherein said 5-(2-aminophenyl)-pyrazole compound is employed in a molar ratio to the cyclizing agent within the range of from about 0.2:1 to about 1:1.

5. The process as defined in claim 4 wherein the reaction of the pyrazole and the cyclizing agent is carried out at a temperature within the range of from about 60° to about 240° C. in the presence of a basic solvent.

6. The process as defined in claim 4 wherein the cyclizing agent is phosgene or ethyl chloroformate so that in the final product produced X is O.

7. The process as defined in claim 4 wherein the cyclizing agent is thiophosgene so that in the final product produced X is S.

8. The process as defined in claim 1 wherein the starting quinolone has the structure

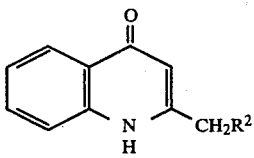

wherein $R^2$ is lower alkoxy, and the cyclizing agent employed is phosgene or ethyl chloroformate, so that the product produced has the structure

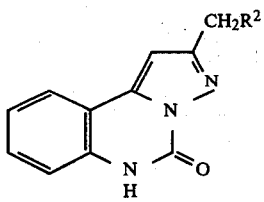

wherein $R^2$ is lower alkoxy.

9. The process as defined in claim 1 wherein the quinolone compound of the structure

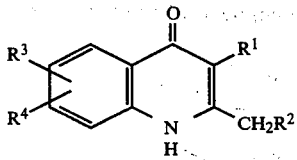

is prepared by reacting an aniline compound of the structure

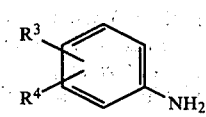

wherein $R^3$ and $R^4$ are as defined above, with a carboxylic acid ester of the structure

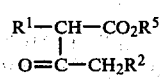

wherein $R^1$ and $R^2$ are as defined above and $R^5$ is lower alkyl, in the presence of an acid medium, to form a crotonate of the structure

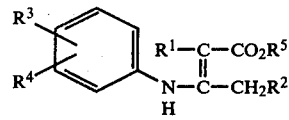

wherein $R^1$, $R^2$, $R^3$, $R^4$ and $R^5$ are as defined above, and reacting the above crotonate with diphenyl ether to form the quinolone compound.

10. The process as defined in claim 9 wherein the starting aniline compound is aniline, and the carboxylic acid ester has the structure

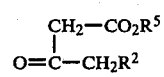

so that the quinolone product produced has the structure

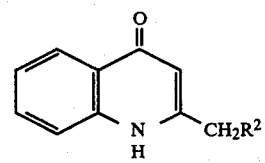

wherein $R^2$ is lower alkoxy.

11. The process as defined in claim 1 wherein the quinolone compound of the structure

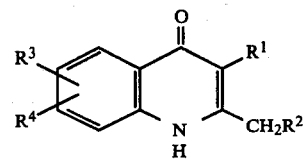

is prepared by reacting an isatoic anhydride of the structure

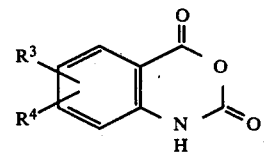

wherein $R^3$ and $R^4$ are as defined above with a carboxylic acid ester of the structure

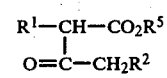

wherein $R^1$ and $R^2$ are as defined above, and $R^5$ is lower alkyl, to form a quinolone of the structure

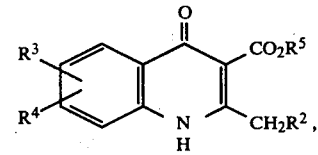

hydrolyzing and neutralizing the above quinolone to form an acid of the structure

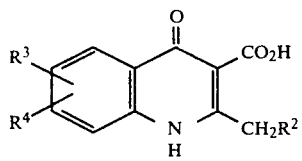

and thereafter decarboxylating the above acid by heating to form the quinolone of the structure

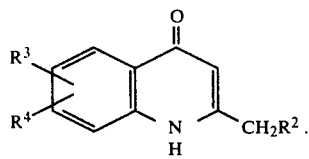

12. A process for preparing pyrazolo[1,5-c]quinazolines of the structure

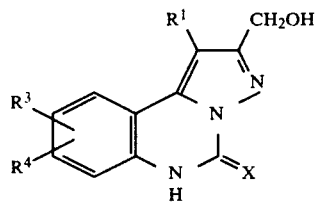

wherein

X is O or S;

$R^1$ is hydrogen, lower alkyl, hydroxymethyl, phenyl-lower alkyl, phenyl or phenyl substituted with halogen, lower alkyl, lower alkoxy, or trifluoromethyl;

$R^3$ and $R^4$ are the same or different and are selected from the group consisting of hydrogen, alkyl of 1 to 4 carbons, alkoxy of 1 to 4 carbons, lower alkanoyloxy of 1 to 4 carbons, nitro, benzyloxy, benzyloxy having a single mono-lower alkoxy substituent, halogen, hydroxy, and trifluoromethyl;

and physiologically acceptable salts thereof, which comprises the steps of reacting a quinazoline compound of the structure

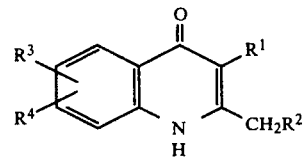

wherein $R^1$, $R^3$ and $R^4$ are as defined above and $R^2$ is lower alkoxy, phenyl-lower alkoxy, phenoxy, or phenoxy substituted with lower alkyl or lower alkoxy; with a hydrazine compound to form a 5-(2-aminophenyl)-pyrazole of the structure

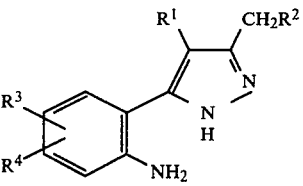

thereafter reacting the above pyrazole with a cyclizing agent of the structure $CXCl_2$ or ethyl chloroformate to form the pyrazolo[1,5-c]quinazoline compound of the structure

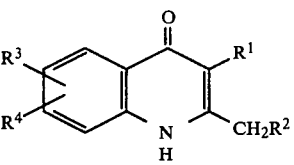

and then reacting the so-formed pyrazolo[1,5-c]quinazoline with a halogen acid to form a reaction product mixture containing

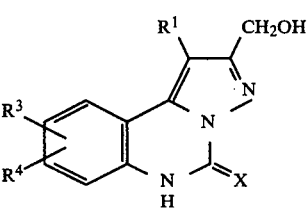

13. The process as defined in claim 12 wherein said halogen acid is HBr, HCl, or HF, and is employed in a molar ratio to the starting quinazoline of within the range of from about 100:1 to about 1:1, and said reaction is carried out at a temperature within the range of from about 20° to about 130° C.

14. The process as defined in claim 12 wherein the product produced is a mixture of

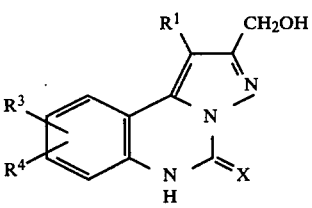

and

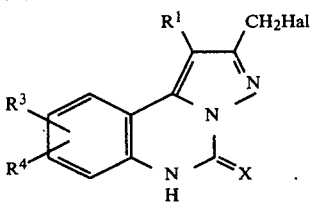

15. The process as defined in claim 14 including the step of heating the mixture of products at a temperature within the range of from about 20° to about 100° C. to convert said mixture of products to

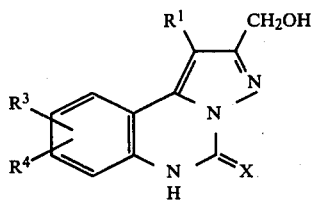

16. The process as defined in claim 12 wherein in the starting quinazoline compound R² is lower alkoxy, and the final product produced has the structure

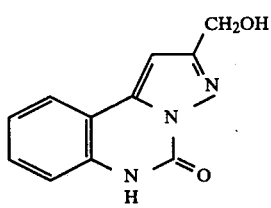

17. A process for preparing quinazolines of the structure

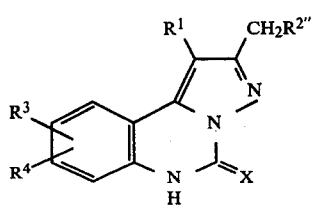

wherein
X is O or S;
R¹ is hydrogen, lower alkyl, hydroxymethyl, phenyl-lower alkyl, phenyl or phenyl substituted with halogen, lower alkyl, lower alkoxy, or trifluoromethyl;
R²″ is lower alkanoyloxy, phenyl-lower alkanoyloxy or benzoyloxy;
R³ and R⁴ are the same or different and are selected from the group consisting of hydrogen, alkyl of 1 to 4 carbons, alkoxy of 1 to 4 carbons, lower alkanoyloxy of 1 to 4 carbons, nitro, benzyloxy, benzyloxy having a single mono-lower alkoxy substituent, halogen, hydroxy, and trifluoromethyl; which comprises reacting a quinazoline compound of the structure

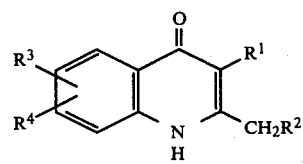

wherein R¹, R³ and R⁴ are as defined above and R² is lower alkoxy, phenyl-lower alkoxy, phenoxy, or phenoxy substituted with lower alkyl or lower alkoxy; with a hydrazine compound to form a 5-(2-aminophenyl)-pyrazole of the structure

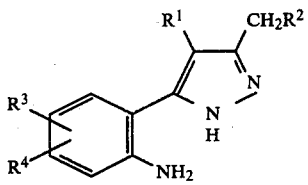

thereafter reacting the above pyrazole with a cycliz agent of the structure

CXCl₂ or ethyl chloroformate to form the pyrazolo[1 c]quinazoline compound of the structure

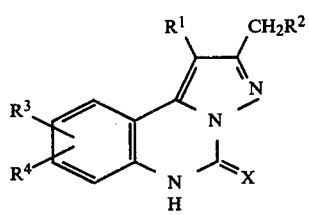

and then reacting the so-formed pyrazolo[: c]quinazoline with a halogen acid to form a react product mixture containing

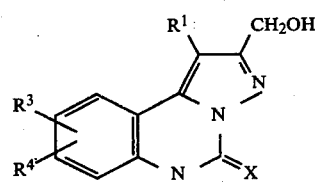

and

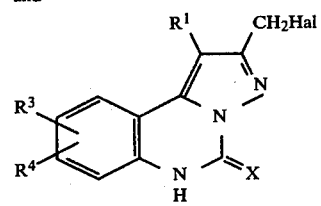

wherein Hal is Cl, Br or F, reacting the above mixt of hydroxymethyl and halomethyl quinazolines wit compound of the structure MR²″ and an acid of structure R²″H wherein M is an alkali metal and R² as defined above.

18. The process as defined in claim 17 wherein in starting materials R¹, R³ and R⁴ are hydrogen and ː O, and R²″ is

19. The process as defined in claim 12 wherein : reaction product mixture also contains a halomei compound of the structure

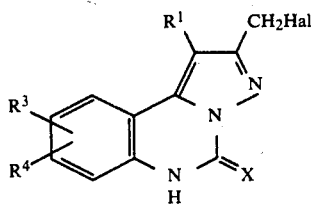

wherein Hal is Cl, Br or F, and further including the steps of heating the reaction product mixture in water at a temperature ranging from about 20° to about 100° C. to convert the halomethyl compound to the corresponding hydroxymethyl compound.

20. The process as defined in claim 12 wherein said reaction product mixture also contains a halomethyl compound of the structure

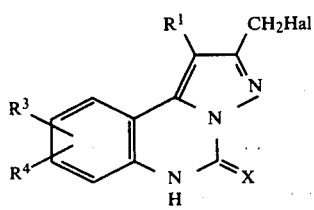

wherein Hal is Cl, Br or F, and further including the step of reacting the reaction product mixture with a compound of the structure

MOCR and an acid of the structure

RCOH wherein M is an alkali metal and R is lower alkyl, phenyl or phenyl-lower alkyl, to form a compound of the structure

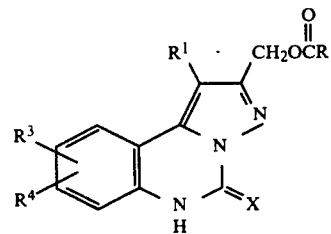

and reacting the above compound with a strong base to form the corresponding hydroxymethyl compound

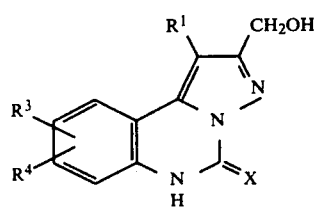

21. A process for preparing pyrazolo[1,5-c]quinazolines of the structure

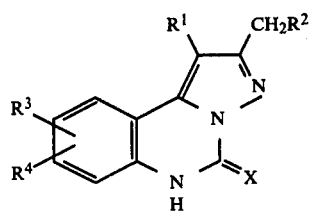

wherein
X is O or S;
R¹ is hydrogen, lower alkyl, hydroxymethyl, phenyl-lower alkyl, phenyl or phenyl substituted with halogen, lower alkyl, lower alkoxy, or trifluoromethyl;
R² is lower alkoxy, phenyl-lower alkoxy, phenoxy, or phenoxy substituted with lower alkyl or lower alkoxy;
R³ and R⁴ are the same or different and are selected from the group consisting of hydrogen, alkyl of 1 to 4 carbons, alkoxy of 1 to 4 carbons, lower alkanoyloxy of 1 to 4 carbons, nitro, benzyloxy, benzyloxy having a single mono-lower alkoxy substituent, halogen, hydroxy, and trifluoromethyl;
and physiologically acceptable salts thereof, which comprises the steps of reacting a quinolone compound of the structure

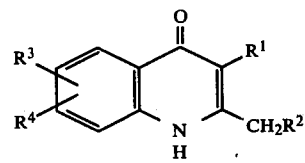

wherein R¹, R², R³ and R⁴ are as defined above, with a hydrazine compound to form a 5-(2-aminophenyl)pyrazole of the structure

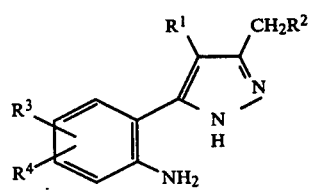

and thereafter reacting the above pyrazole with ethyl chloroformate to form the pyrazolo[1,5-]quinazoline compound of the structure

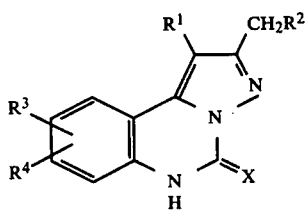

22. A process for preparing pyrazolo[1,5-c]quinazolines of the structure

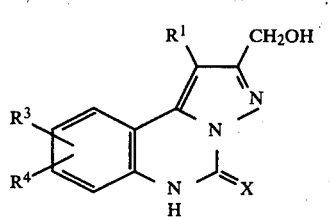

wherein

X is O or S;

R¹ is hydrogen, lower alkyl, hydroxymethyl, phenyl-lower alkyl, phenyl or phenyl substituted with halogen, lower alkyl, lower alkoxy, or trifluoromethyl;

R³ and R⁴ are the same or different and are selected from the group consisting of hydrogen, alkyl of 1 to 4 carbons, alkoxy of 1 to 4 carbons, lower alkanoyloxy of 1 to 4 carbons, nitro, benzyloxy, benzyloxy having a single mono-lower alkoxy substituent, halogen, hydroxy, and trifluoromethyl;

and physiologically acceptable salts thereof, which comprises the steps of reacting a quinazoline compound of the structure

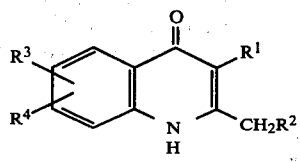

wherein R¹, R³ and R⁴ are as defined above and R² is lower alkoxy, phenyl-lower alkoxy, phenoxy, or phenoxy substituted with lower alkyl or lower alkoxy; with a hydrazine compound to form a 5-(2-aminophenyl)-pyrazole of the structure

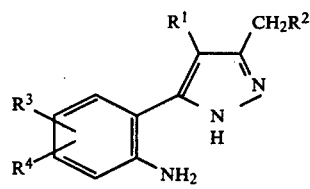

thereafter reacting the above pyrazole with ethyl chloroformate to form the pyrazolo[1,5-c]quinazoline compound of the structure

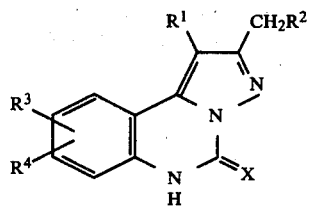

and then reacting the so-formed pyrazolo[1,5-c]quinazoline with a halogen acid to form a reaction product mixture containing

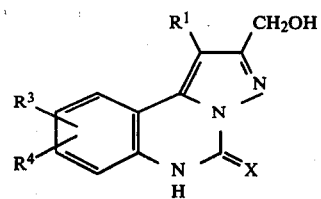

* * * * *

UNITED STATES PATENT AND TRADEMARK OFFICE
CERTIFICATE OF CORRECTION

PATENT NO. : 4,252,945
DATED : February 24, 1981
INVENTOR(S) : Richard A. Conley et al.

It is certified that error appears in the above-identified patent and that said Letters Patent are hereby corrected as shown below:

Column 10, Table A, Column IV, the structure in the heading should read

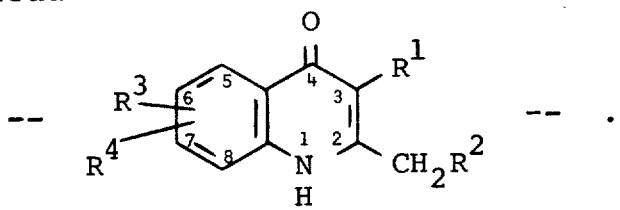

Column 10, line 42, "quinoline" should read --quinolone--.
Column 12, Table B, Column III, under heading "X" insert -- _____/ --.
    as in Col. II Column 12, Table B, Column III, under headings "$R^1$ $R^2$" insert -- _____/ --.
    as in Col. I Column 18, lines 20-25, the structure should read

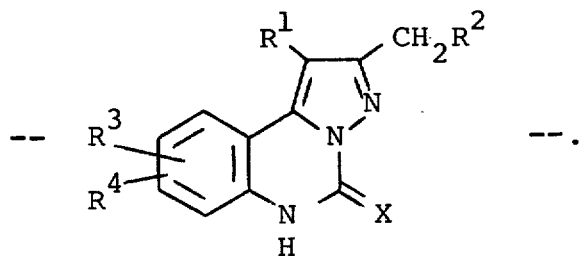

UNITED STATES PATENT AND TRADEMARK OFFICE
CERTIFICATE OF CORRECTION

PATENT NO. : 4,252,945
DATED : February 24, 1981        Page 2 of 2
INVENTOR(S) : Richard A. Conley et al.

It is certified that error appears in the above-identified patent and that said Letters Patent are hereby corrected as shown below:

Column 20, line 11, "cycliz" should read --cyclizing--.
Column 20, line 16, "pyrazolo[" should read --pyrazolo[1,5- --.
Column 20, line 29, "pyrazolo[" should read --pyrazolo[1,5- --.
Column 20, line 30, "react" should read --reaction--.
Column 20, line 52, "mixt" should read --mixture--.
Column 20, line 53, "wit" should read --with a--.
Column 20, line 54, at the end of the line insert --the--.
Column 20, line 55, "R" should read --$R^2$" is--.

Column 20, line 57, at the end of the line insert --the--.
Column 20, line 58, at the end of the line insert --X is--.
Column 20, line 66, at the end of the line insert --said--.
Column 20, line 67, "halome" should read --halomethyl--.
Column 22, line 55, "[1,5-" should read --[1,5-c--.

Signed and Sealed this

Thirtieth Day of June 1981

[SEAL]

Attest:

RENE D. TEGTMEYER

Attesting Officer     Acting Commissioner of Patents and Trademarks